United States Patent
McCauley et al.

(10) Patent No.: US 10,430,556 B2
(45) Date of Patent: Oct. 1, 2019

(54) LOCATION TRIGGERING FOR PRESCRIPTION READY NOTIFICATIONS

(71) Applicant: WALGREEN CO., Deerfield, IL (US)

(72) Inventors: Tim McCauley, Evanston, IL (US);
Jon Turkington, Huntley, IL (US);
Abhinav Dhar, Naperville, IL (US);
Dejan Kozic, Wadsworth, IL (US);
Nicholas Eby, Downers Grove, IL (US)

(73) Assignee: WALGREEN CO., Deerfield, IL (US)

( * ) Notice: Subject to any disclaimer, the term of this patent is extended or adjusted under 35 U.S.C. 154(b) by 211 days.

(21) Appl. No.: 14/249,492

(22) Filed: Apr. 10, 2014

(65) Prior Publication Data
US 2015/0294084 A1    Oct. 15, 2015

(51) Int. Cl.
*G06F 19/00* (2018.01)
*H04W 4/02* (2018.01)
*H04W 40/24* (2009.01)

(52) U.S. Cl.
CPC ........ *G06F 19/3456* (2013.01); *G06F 19/328* (2013.01); *H04W 4/023* (2013.01); *H04W 40/244* (2013.01)

(58) Field of Classification Search
None
See application file for complete search history.

(56) References Cited

U.S. PATENT DOCUMENTS

| | | | |
|---|---|---|---|
| 8,626,530 B1 * | 1/2014 | Tran | G06F 19/3456 705/2 |
| 8,758,238 B2 * | 6/2014 | Clapp | G06F 19/327 128/920 |
| 9,430,781 B1 | 8/2016 | Kerr et al. | |
| 2002/0128863 A1 * | 9/2002 | Richmond | G06F 19/328 705/2 |

(Continued)

OTHER PUBLICATIONS

U.S. Appl. No. 14/530,179, filed Oct. 31, 2014.
(Continued)

*Primary Examiner* — Elaine Gort
*Assistant Examiner* — Rachelle L Reichert
(74) *Attorney, Agent, or Firm* — Marshall, Gerstein & Borun LLP; Randall G. Rueth

(57) ABSTRACT

Methods, systems, and apparatus are disclosed to notify and route a customer to a prescription pickup location. A communication device detects the proximity of a prescription customer to an associated pharmacy location. The customer is then notified when the prescription is available at the pharmacy location based on identifying customer information and the location information. Once the pharmacy location is detected, the communication device sends the identifying customer information and the location information to a pharmacy computing device. The communication device then displays a notification that a prescription is available for the prescription customer at the pharmacy based on a determination made by the pharmacy computing device using the location information and the identification infor- (Continued)

mation. In addition, the communication device can display a map of the pickup location, various prompts to the customer to establish payment and/or to determine whether the customer has questions for pharmacy staff.

25 Claims, 7 Drawing Sheets

(56) References Cited

U.S. PATENT DOCUMENTS

| | | | | |
|---|---|---|---|---|
| 2003/0028399 | A1* | 2/2003 | Davis | G06F 19/327 705/2 |
| 2005/0136845 | A1* | 6/2005 | Masuoka | G01S 5/0294 455/67.14 |
| 2007/0184852 | A1* | 8/2007 | Johnson | H04W 64/00 455/456.1 |
| 2008/0059227 | A1* | 3/2008 | Clapp | G06F 19/327 705/2 |
| 2010/0020776 | A1* | 1/2010 | Youssef | H04W 64/00 370/338 |
| 2010/0098036 | A1* | 4/2010 | Li | H04W 4/20 370/338 |
| 2010/0161356 | A1* | 6/2010 | Louie | G06F 19/328 705/3 |
| 2011/0028161 | A1* | 2/2011 | Larsen | G01S 5/0226 455/456.1 |
| 2011/0166878 | A1* | 7/2011 | Louie | G06F 19/327 705/2 |
| 2011/0221568 | A1* | 9/2011 | Giobbi | G06F 19/322 340/5.82 |
| 2011/0257989 | A1* | 10/2011 | Kumar | G06Q 10/06 705/2 |
| 2012/0115512 | A1* | 5/2012 | Grainger | G01S 5/0257 455/456.3 |
| 2012/0185263 | A1* | 7/2012 | Emert | G06Q 50/22 705/2 |
| 2012/0239417 | A1* | 9/2012 | Pourfallah | G06Q 30/0601 705/2 |
| 2012/0253831 | A1* | 10/2012 | John | G06Q 40/00 705/2 |
| 2013/0006663 | A1* | 1/2013 | Bertha | G06Q 10/10 705/3 |
| 2013/0256403 | A1* | 10/2013 | MacKinnon | G06K 5/00 235/375 |
| 2013/0317944 | A1* | 11/2013 | Huang | G01S 5/0252 705/26.61 |
| 2014/0074743 | A1* | 3/2014 | Rademaker | G06Q 50/28 705/334 |
| 2014/0089111 | A1* | 3/2014 | Fernandez | G06Q 30/0633 705/15 |
| 2014/0278466 | A1* | 9/2014 | Simmons | G06F 19/3456 705/2 |
| 2015/0095161 | A1* | 4/2015 | Goel | G06Q 30/0267 705/14.64 |
| 2015/0221010 | A1* | 8/2015 | Ming | G06Q 30/0623 705/26.61 |

OTHER PUBLICATIONS

U.S. Appl. No. 13/286,909, filed Nov. 1, 2011.
U.S. Appl. No. 14/288,087, filed May 27, 2014.
U.S. Appl. No. 14/249,492, filed Apr. 10, 2014.
U.S. Appl. No. 14/249,492, Final Office Action, dated Jul. 14, 2016.
U.S. Appl. No. 14/249,492, Nonfinal Office Action, dated Feb. 19, 2016.
U.S. Appl. No. 14/456,713, filed Aug. 11, 2014.
U.S. Appl. No. 14/526,887, filed Oct. 29, 2014.
U.S. Appl. No. 14/530,179, Nonfinal Office Action, dated May 17, 2017.
U.S. Appl. No. 15/142,557, filed Apr. 29, 2016.

\* cited by examiner

LOCATION TRIGGERING FOR PRESCRIPTION READY NOTIFICATIONS

TECHNICAL FIELD

The present disclosure relates generally to prescription transactions at a pharmacy and, more particularly, to coordinating prescription pickup locations between customers and pharmacy staff.

BACKGROUND

In many cases, a pharmacy customer will order a prescription refill in advance of his or her visit to the pharmacy to pick up the refill. In other cases, a prescription for an initial supply may, for example, have already been called in by the customer's doctor. Generally, the customer's order will then be filled, packaged, and stored until the customer visits the pharmacy to pick up the order. Many pharmacies store such an order in a common area along with other customers' orders that have also been placed in advance of those customers' visits to the pharmacy.

Upon arriving at the pharmacy, the customer generally proceeds to a point of sale area, such as a prescription pick-up window, a drive-thru window, etc., and identifies himself or herself to a pharmacy technician or other on-duty employee. The pharmacy technician then locates and retrieves the customer's previously prepared order from the common storage area. In some cases, the pharmacy technician may ask the customer for further verification of his or her identity before the pharmacy technician retrieves the customer's order. Additionally, in some cases, the pharmacy technician and customer may review information about the customer's refill, and/or information about the customer's insurance coverage. The customer may then pay for and receive the refill.

To make the prescription pickup and payment process more convenient for the customer, some pharmacies have implemented express pickup and/or payment services. Express pickup services typically allow a customer to register their identification, insurance information, and/or other applicable information with the pharmacy so this information does not need to be initially provided (but may simply be verified) when the customer picks up the prescription. Express pay services likewise allow a customer to register a form of payment (e.g., a debit or credit card) for prescriptions so payments can be processed before the customer picks up the prescription. Pharmacies often locate the express pickup counter, standard pickup counter and drive-thru pickup locations separate from one another.

Although express pickup and payment procedures and drive-thru options provide more convenience to the customer, these prescription pickup procedures can be further improved upon. First, a customer does not know if his or her prescription is ready until going to the applicable counter and asking pharmacy staff. If the counter already has a line, the customer may need to wait unnecessarily only to be informed that the prescription is not available, and then wait again until the prescription is ready. Second, since the express pickup, standard pickup, and drive-thru locations are generally in separate areas, a customer may go the wrong location or not know where to go to initially pick up the prescription. Third, the type of prescription may prevent the customer from picking up the prescription at the express counter or at the drive-thru and/or the customer might have questions that cannot be addressed at these locations. As a result, keeping both the pharmacy staff and the customer informed of the proper pharmacy pickup location is important and presents several challenges.

SUMMARY

In some embodiments, a method includes detecting proximity of the first communication device to a pharmacy location and sending prescription customer identification information and pharmacy identification information to a pharmacy computing device. The method further includes displaying a notification that a prescription is available for the prescription customer at the pharmacy based on a determination made by the pharmacy computing device using the prescription customer identification information and pharmacy identification information. In addition, the method also includes displaying another notification including an indication of a prescription pickup location within the pharmacy based on whether the determination made using the prescription customer identification information and pharmacy identification information.

In additional embodiments, methods, systems and apparatus are described that include detecting the proximity of a first communication device to one or more other second communication devices, which could be positioned within (or in proximity to) any suitable building, such as a retail store, a doctor's office, a hospital, etc. In such embodiments, a communication device displays a first notification that the first communication device has entered (or is proximate to) the building based on the proximity of the first communication device to a second communication device within (or proximate to) the building. Further variations of these embodiments include the first communication device performing context-based actions in response to the detected proximity. Context-based actions could include actions in regards to a healthcare or a non-healthcare environment. For example, context-based actions could include the first communication device sending information identifying a registered user, which could be a prescription customer, a retail customer, a healthcare patient, etc., to a computing device. In addition, the embodiment includes the first communication device displaying a second notification based on one or more indications received from the computing device based on the particular context-based actions. For example, the second notification could include one or more coupons, an indication that a doctor is ready to see the patient, etc. Furthermore, in such an embodiment, the second notification and/or one or more additional notifications could include other information relevant to the particular context-based action. For example, the second notification and/or one or more additional notifications could include a map of the doctor's office within a building, a room within a hospital, a retail sale item location, etc.

In other embodiments, a non-transitory computer readable media includes instructions stored in a communications device, that when executed by a processor cause the processor to detect a proximity of the communication device to a pharmacy location and to send pharmacy identification information and customer identification information to the pharmacy computing device. The non-transitory computer readable media includes further instructions to display a notification that a prescription is available for the prescription customer at the pharmacy based on a determination made by the pharmacy computing device and to display another notification of the prescription pickup location within the pharmacy based on the determination made by the pharmacy computing device.

In yet other embodiments, a method includes displaying a first notification that the first communication device has entered a pharmacy based on detecting a proximity of the first communication device to a second communication device within the pharmacy. The method further includes sending information identifying the prescription customer and the pharmacy location to a pharmacy computing device. In addition, the method includes displaying a second notification based on an indication received from the pharmacy computing device that a prescription is ready at a prescription pickup location within the pharmacy based on the information and displaying a map of the prescription pickup location.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, whenever possible, the following description refers to the reference numerals included in the following figures, in which features depicted in multiple figures are designated with consistent reference numerals.

DETAILED DESCRIPTION

The following text sets forth a detailed description of numerous different embodiments. However, it should be understood that the detailed description is to be construed as exemplary only and does not describe every possible embodiment since describing every possible embodiment would be impractical. One of ordinary skill in the art will recognize, in light of the teaching and disclosure herein, that numerous alternative embodiments could be implemented.

Although the embodiments described throughout the disclosure are explained in the context of a pharmacy, other embodiments of the present disclosure include both healthcare and non-healthcare contexts. For example, in some embodiments, the notifications received at a communication device include information relevant to the availability, payment, and pickup location of a prescription. But in other embodiments, the proximity detection as further described herein could trigger notifications relevant to a patient's visit to a doctor's office and/or a hospital. In addition, the proximity detection could trigger notifications relevant in a non-healthcare context. For example, a communication device could receive one or more coupons that are relevant to a particular retail location and/or the location of one or more retail sale items within a particular store.

It should be understood that, unless a term is expressly defined in this patent application using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent application.

Figure 1:
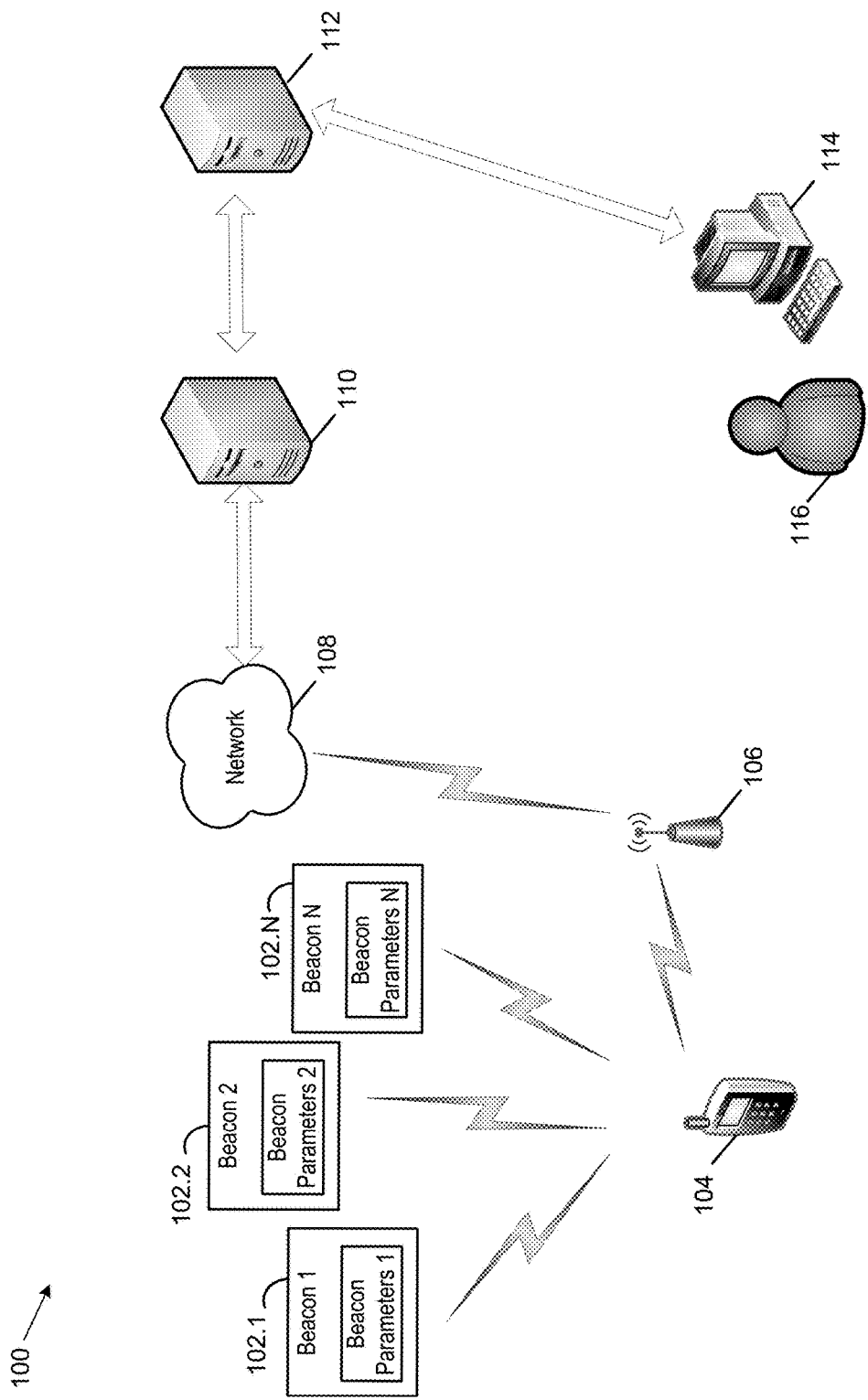
FIG. 1 is a block diagram of an exemplary system 100 for informing a customer that a prescription is ready and where to pick up the prescription within a pharmacy, according to an embodiment.

FIG. 1 is a block diagram of an exemplary system 100 for informing a customer that a prescription is ready and where to pick up the prescription, which could be within a pharmacy or associated with the pharmacy (e.g., a drive-thru window), according to an embodiment. System 100 includes 'N' number of communication devices 102.1-102.N, a communication device 104, a base station 106, a network 108, a server 110, a pharmacy computing system 112, and a pharmacy computer terminal 114, which may be operated by a user 116 (e.g., a pharmacist and/or a pharmacy technician).

Advantageously, the system 100 may provide the identification of the customer to user 116 shortly after an arrival of the customer at the pharmacy, and thereby allow the user to obtain the customer's previously prepared prescription while the customer completes other aspects of his or her transaction. The prescription may then be ready to be handed to the customer at a pharmacy pick-up area, such as a prescription pick-up window, upon payment, without the customer having to unnecessarily wait for the pharmacy technician to find the prescription. The indication that the customer has come to the pharmacy to pick up his or her prescription may be generated and provided to the pharmacy technician before an arrival of the customer at the pharmacy pick-up area or other point of sale. Example techniques for identifying the customer and providing the advance indication to the pharmacy technician, and examples of further advantages of one or more embodiments disclosed herein, are discussed further below.

Generally, the system 100 may be used to provide a pharmacy employee with an advance identification of a customer who has arrived at the pharmacy to pick up a previously prepared pharmacy order and/or the location where the customer expects to pick up the prescription. The previously prepared pharmacy order may be a refill of a prescription medication that the customer has called in ahead of time. Alternatively, the customer may have ordered the refill online, via text message, etc. With respect to the previously ordered refill, each of a drug utilization review, a drug interaction review, a confirmation of the customer's insurance coverage, a confirmation of the name and dosage of the medication, etc. may have already been performed by the time the customer arrives at the pharmacy to pick up the refill.

In some embodiments, the customer may be picking up a prescription refill. In other embodiments, the customer may additionally or alternatively be picking up a prescribed pharmaceutical product which is not a refill, including, for example, an initial supply of a prescribed pharmaceutical product which the customer has not used before. The prescription for the initial supply may, for example, have already been called in by the customer's doctor.

Communication devices 102.1-102.N are each configured to communicate with communication device 104 and to store respective beacon parameters 1 through N. In an embodiment, communication devices 102.1-102.N are positioned at various locations within or proximate to a pharmacy. For example, communication device 102.1 could be placed near the main entrance or drive-thru entrance of the pharmacy while communication device 102.2 is placed in an aisle.

The beacon parameters 1 through N can be stored in any suitable memory device utilized by the respective communication device 102, such as a flash-based memory, a battery-backed RAM, etc. In some embodiments, communication devices 102.1-102.N are configured to broadcast beacons in accordance with one more communication protocols and/or standards, such as IEEE Standards, for example. In other embodiments, the beacon parameters are not broadcasted. For example, non-broadcasting embodiments could include those embodiments whereby one or more of communication devices 102.1-102.N emits audible and/or inaudible sounds.

In other embodiments, communication devices 102.1-102.N are not implemented as iBeacons, but as other suitable communication devices and/or emitters configured to transmit their respective locations, sounds, etc. in accordance with any suitable identifier and/or communication protocol. In some embodiments, communication devices 102.1-102.N may be configured to transmit their respective location beacons in accordance with a communication protocol, such as radio frequency identification (RFID) and/or a near field communication (NFC) protocols. To provide another example, communication devices 102.1-102.N may be configured to transmit their respective location beacons in accordance with a Wi-Fi communication protocol. Wi-Fi protocols could include ad-hoc communications, such as Wi-Fi direct, for example, such that direct communications is facilitated between communication devices 102.1-102.N and communication device 104.

In other embodiments, communication devices 102.1-102.N may be configured to transmit their respective location beacons in accordance with a suitable unique identifier that may be correlated and identified by another communication device receiving the location beacon. For example, communication devices 102.1-102.N may be configured to transmit their respective location beacons as part of one or more emitted sounds. Examples of emitted sounds could include one or more tones and/or music that may be readily identified with a physical location once received and processed by another communication device. In various embodiments, the sounds include those that are inaudible to people and or animals as well as emitted sounds that are audible (e.g., in-store music).

In accordance with embodiments in which one or more of communication devices 102.1-102.N broadcast beacon parameters, each beacon broadcasted by its respective communication device 102 includes its respective beacon parameters. As will be appreciated by those of ordinary skill in the relevant art(s), communication devices 102.1-102.N may be implemented with any suitable number of power sources, wireless transmitters, receivers, and/or transceivers, processors, memories, etc., to facilitate this functionality. In some embodiments, communication devices 102.1-102.N are implemented as iBeacons, which have been developed by Apple, Inc. In accordance with such an embodiment, communication devices 102.1-102.N are configured to transmit their respective location beacons in accordance with one or more standards utilized by iBeacon devices. For example, communication devices 102.1-102.N may transmit their respective beacon parameters in accordance with a BLUETOOTH Low Energy (BLE) protocol, which implements the BLUETOOTH 4.0 specification at the time of this writing.

In some embodiments, communication devices 102.1-102.N are configured to only transmit their respective location beacons and to not otherwise receive communications. In other embodiments, communication devices 102.1-102.N are configured to transmit their respective location beacons and to receive communications from other communication devices, such as communication device 104, for example. Embodiments in which communication devices 102.1-102.N only transmit their respective location beacons could be particularly useful when they are implemented as devices that utilize a battery power source, as such a configuration advantageously reduces power consumption.

The beacon parameters 1 through N can include any suitable identification of the location and/or identity of each respective communication device 102.1-102.N. In some embodiments, beacon parameters 1 through N include latitude and longitude coordinates. In accordance with such embodiments, the beacon parameters 1 through N may be pre-programmed into the respective communication device 102 and/or obtained by a communication device 102 via a suitable positioning system. Pre-programming embodiments could be particularly useful when the communication devices 102 are placed at fixed locations within a pharmacy in a semi-permanent or permanent manner, such that the coordinates do not need to be substantially changed over time.

In some embodiments, communication devices 102.1-102.N can include any suitable number of global navigation satellite system (GNSS) and/or other suitable types of receivers to obtain a geographic location. For example, communication devices 102.1-102.N can be configured to determine their respective position via network triangulation. Such embodiments could be particularly useful when the locations of the communication devices could change over time, allowing the respective beacon parameters transmitted by each respective communication device 102 to reflect these changes.

In other embodiments, beacon parameters 1 through N do not include actual location coordinates, but include other types of information. This information could include, for example, information identifying the communication device and/or a calibrated receive power information. For example, beacon parameters 1 through N could include unique identifiers that identify each communication device 102.1-102.N. In an embodiment, beacon parameters 1 through N are implemented as proximity universally unique identifiers (UUIDs) in accordance with an iBeacon format or other suitable format. In accordance with such embodiments, the beacon parameters could include other identifiers. For example, a portion of the beacon parameters could correspond to a pharmacy location and be common among all communication devices 102.1-102.N positioned within a single pharmacy, while another portion of the beacon parameters may function to uniquely identify each communication device 102.

Further in accordance with such embodiments, beacon parameters 1 through N additionally or alternatively include calibrated receive power information. For example, iBeacons broadcast a power value that is a calibrated received signal strength indicator (RSSI) measured 1 meter from the communication device by another communication device. By broadcasting this calibrated receive power value, another device (e.g., communication device 104) can compare the RSSI of the received beacon to the calibrated value and use this ratio to estimate its proximity to the communication device transmitting the beacon.

Communication device 104 is configured to communicate with one or more of communication devices 102.1-102.N and/or to receive emitted identifiers from one or more of communication devices 102.1-102.N. Communication device 104 is configured to communicate with network 108 via base station 106. As will be appreciated by those of ordinary skill in the relevant art(s), communication device 104 may be implemented with any suitable number of power sources, wireless transmitters, receivers, and/or transceivers, processors, memories, microphones, etc., to facilitate this functionality. In an embodiment, communication device 104 is implemented as a user equipment (UE), such as a smartphone, for example. Although communication device 104 is illustrated in FIG. 1 as a phone, communication device 104 may be implemented as any suitable communication device configured to communicate with communication devices 102.1-102.N and network 108. For example, communication device 104 could be implemented as a personal digital assistant (PDA), a tablet computer, a laptop computer, etc.

Communication device 104 is configured to communicate with base station 106 via any suitable communications protocol to access network 108, such as cellular or Wi-Fi protocols, for example. Communication device 104 is configured to receive location beacons transmitted by any of communication devices 102.1-102.N to detect its proximity to a respective communication device 102. In an embodiment in which communication devices 102.1-102.N are implemented as iBeacon devices, communication device 104 can determine its proximity to a respective communication device 102 via an RSSI measurement of the transmitted location beacon and a comparison of the RSSI to the calibrated RSSI signal transmitted by the respective communication device 102.

In accordance with other embodiments in which communication devices 102.1-102.N are not implemented as iBeacon devices, communication device 104 is configured to detect its proximity to a respective communication device 102 using any suitable proximity detection method. As will be appreciated by those of ordinary skill in the relevant art(s), proximity detection can be accomplished using any suitable known ranging methods, such as signal attenuation measurement and/or propagation time of arrival (ToA) and time of departure (ToD) timestamping techniques. To provide another example, in various embodiments communication device 104 may detect its proximity to a respective communication device 102 by listening to one or more sounds emitted from the respective communication device.

In various embodiments, communication device 104 is configured to connect to a respective communication device 102 once a beacon and/or other emission (e.g., a sound) transmitted by the respective communication device 102 is detected. Once communication device 104 connects to the respective communication device 102, communication device 104 is configured to receive that communication device's respective beacon parameters. Communication device 104 is configured to launch one or more applications upon detection of a beacon and/or upon receiving the beacon parameters. In an embodiment, the one more applications can be launched as a background application and do not require user intervention. The one more applications allow the communication device 104 to use the beacon parameters to determine that the communication device is at a corresponding pharmacy location.

In an embodiment, communication device 104 is configured to locally store a correlation of beacon parameters and their corresponding pharmacy locations and/or a correlation of emitted sounds and their corresponding pharmacy locations. For example, upon installation of an application, communication device 104 could download and store a list of pharmacy locations and their associated identifiers (e.g., UUIDs) corresponding to the communication devices 102 at each of the pharmacy locations. Once communication device 104 connects to a communication device 102, identifiers included in the received beacon parameters can be referenced to this list so communication device 104 can verify whether communication device 104 is at a corresponding pharmacy location.

In some embodiments, communication device 104 communicates with server 110 and/or pharmacy computing system 112 via network 108 to pass the received identifier information and/or received sounds to server 110 and/or pharmacy computing system 112. In accordance with these embodiments, server 110 and/or pharmacy computing system 112 then determines whether the received identifying information and/or sounds match a pharmacy location. If server 110 and/or pharmacy computing system 112 find a matching pharmacy location, then server 110 and/or pharmacy computing system 112 can send this location back to communication device 104. In this way, communication device 104 can offload the pharmacy lookup functionality to server 110 and/or pharmacy computing system 112. These embodiments could be particularly useful when, for example, processing power and/or memory is sought to be conserved at communication device 104.

In other embodiments, communication device 104 communicates with one more of communication devices 102.1-102.N, which in turn may pass the received identifier information and/or received sounds to server 110 and/or pharmacy computing system 112. In accordance with these embodiments, one or more of communication devices 102.1-102.N, server 110, and/or pharmacy computing system 112 then determines whether the received identifying information and/or sounds match a pharmacy location. If one or more of communication devices 102.1-102.N, server 110, and/or pharmacy computing system 112 find a matching pharmacy location, then server 110 and/or pharmacy computing system 112 can send this location back to communication device 104.

As will be appreciated by those of ordinary skill in the relevant art(s), one more of communication devices may receive data from communication device 104 to determine a matching pharmacy location using any suitable communication system. For example, one or more of communication devices 102.1-102.N may be configured to communicate with communication device 104 using one or more application programming interfaces (APIs).

In various embodiments, communication device 104 is configured to display one or more notifications that a location beacon has been detected and/or the corresponding pharmacy location. In this way, communication device 104 can alert a customer that he is within or near a pharmacy when communication device 104 detects its proximity to a communication device 102. For example, if a communication device 102 is positioned near an entrance of a pharmacy, then a customer can be alerted as soon as he walks into the pharmacy that the application has determined the pharmacy location. To provide another example, if a customer is already parking in the pharmacy parking lot and does not realize there is a drive-thru option available, the customer can be alerted before she gets out of her car that the application has determined the pharmacy location.

In an embodiment, once the pharmacy location is determined, communication device 104 is configured to pass customer information to one or more of communication devices 102.1-102.N, server 110 and/or pharmacy computing system 112 as part of an application programming interface (API) services call utilizing the launched application. Again, the API services call can occur as a background process without user intervention that is triggered upon receipt of a location beacon or other suitable transmission by communication device 104. The customer information can include any suitable information for uniquely identifying the prescription customer. This information could include, for example, any combination of the customer's last name, phone number, date of birth, etc.

In various embodiments, the customer information is entered by a customer upon installation of the application, through a registration process via a website, over the phone, etc. The customer information could form part of a customer profile that is created when the customer initially registers for prescription services, for example. To provide another example, the customer profile could form part of a user profile that is implemented by the operating system installed on the communication device and entered by a user as part of an initial device setup, account setup, user setup, etc.

The customer information may be different based on a particular application. For example, in a pharmacy-based context, the customer information could include allergy information in addition to the customer's contact information. To provide another example, in non-pharmacy embodiments, the information could include a customer's doctor contact information. In non-healthcare embodiments, the information could include a customer's preferred activities and/or hobbies, age, other demographic information, etc., so more relevant coupons can subsequently be generated and sent to the customer using this pre-registered information.

In embodiments in which communication device 104 determines the location of the pharmacy from the beacon parameters, communication device 104 can also pass the pharmacy location information (e.g., a store number and/or physical address) to server 110 and/or pharmacy computing system 112 as part of the API services call or as part of other communications with server 110 and/or pharmacy computing system 112, via base station 106. Based on the customer information and/or pharmacy location information, communication device 104 can display additional notifications regarding the availability of the prescription, where to pick up the prescription, and/or how to pay for the prescription. In addition, communication device 104 can display one or more interactive prompts providing a customer an opportunity to bypass an express pickup location if the customer has questions and wishes to speak to a pharmacist at a full service counter location instead of the express pay location. The conditions upon which these notifications and prompts are generated and displayed are further discussed below.

Base station 106 is configured to facilitate communications between communication device 104 and network 108. Although base station 106 is illustrated in FIG. 1 as wirelessly communicating with network 108, embodiments include communication device 104 providing communications to network 108 via any suitable number of wired and/or wireless links. For example, base station 106 can be coupled to network 108 via one or more landline, internet service provider (ISP) backbone connections, satellite links, a public switched telephone network (PSTN), etc. In various embodiments, base station 106 can be implemented as an access point (AP), a macrocell, a femtocell, etc.

Network 108 includes any suitable number of nodes, additional wired and/or wireless networks, etc., in various embodiments. For example, in an embodiment, network 108 is implemented as a local area network (LAN), or a suitable combination of local and/or external network connections. In various embodiments, network 108 provides communication device 104 connectivity to network services, such as Internet services and/or access to server 110 and/or pharmacy computing system 112. Although one server 110 is shown in FIG. 1, network 108 can include connections to any suitable number of remote devices, servers, nodes, terminals, etc.

Server 110 is configured to communicate with communication device 104 via network 108 and base station 106. Server 110 is configured to communication with pharmacy computing system 112. In various embodiments, server 110 is a web server, a cloud server, etc. Server 110 is configured to perform any portion of processing operations otherwise performed by communications device 104. Server 110 can include any suitable number of processors, memories, databases, etc., to facilitate this functionality.

In an embodiment, server 110 is configured to read data from and write data to pharmacy computing system 112. Server 110 is configured to generate notifications to be sent to communication device 104 based on the customer information and/or location information received from communication device 104 and/or data accessed from pharmacy computing system 112. In accordance with an embodiment, server 110 is configured to generate and send push notifications via network 108 to communication device 104. As previously discussed with reference to the one or more links between base station 106 and network 108, communications between server 110 and network 108 and pharmacy computing system 112 can be implemented with any suitable number of wired and/or wireless links.

Pharmacy computing system 112 is configured to communicate with server 110 and pharmacy computer terminal 114. Although FIG. 1 illustrates pharmacy computer system 112 as having a direct connection to server 110, various embodiments include pharmacy computer system 112 being connected to server 110 via network 108. Pharmacy computing system 112 is configured to store and/or access customer and prescription information from one or more databases, which may be integrated as a part of pharmacy computer system 112 or external to pharmacy computer system 112. Customer and prescription information could include, for example, customer contact information, customer insurance information, a customer's past and current prescriptions, a pharmacy location of each of the customer's current prescriptions, payment information, customer physicians, a customer's preferred pharmacy location, emergency contact information, allergy information, etc. In various embodiments, a user 116 can access pharmacy computer system 112 to query this information, run reports, determine prescription inventory and their corresponding locations, etc.

In an embodiment, pharmacy computer system 112 is implemented as the Walgreen Company's Intercom Plus (IC+) proprietary pharmacy computer system. Because data stored and/or accessed by pharmacy computer system 112 can include private medical record information, embodiments of pharmacy computer system 112 are implemented utilizing secure data storage and access procedures. As previously discussed with reference to the one more links between base station 106 and network 108, communications between pharmacy computer system 112 and pharmacy computer terminal 114 can be implemented with any suitable number of wired and/or wireless links.

Pharmacy terminal 114 is configured to communicate with pharmacy computer system 112 to allow a user 116 to query and/or update customer and/or prescription information. For example, a user 116 (e.g., a pharmacist) may utilize pharmacy terminal 114 at a pharmacy counter location to lookup a customer's prescription. To provide another example, a user 116 can use pharmacy terminal 114 to enable store-to-store prescription filling and/or to transfer prescriptions between pharmacies. In an embodiment, pharmacy terminal 114 provides user 116 with secure access to pharmacy computer system 112. For example, pharmacy terminal 114 can facilitate secure sign on and/or authentication procedures to control access to pharmacy computer system 112.

In an embodiment, server 110 responds to an API services call received from communications device 104 by verifying the status of the prescription with pharmacy computer system 112. In various embodiments, server 110 receives API service calls and verifies information via pharmacy computer system 112 via one or more secure channels. For example, communication device 104 can place API service calls to server 110 via a designated secure url implementing one or more encryption layers, and server 110 can implement a similar designated secure channel for communications with pharmacy computer system 112.

Again, once server 110 receives the API service call, server 110 obtains the customer's identification information. Furthermore, if a beacon identifier that triggered the AP services call is also sent by communication device 104 (e.g., communication device 104 offloads location determination to server 110) then server 110 can also determine the customer's pharmacy location. In embodiments in which communication device 104 calculates the customer's location, server 110 may receive this location separately or as part of the API service call.

In an embodiment, server 110 communicates with pharmacy computer system 112 to determine the status of the prescription. In other words, by communicating with pharmacy computer system 112, server 110 can determine whether a prescription corresponding to a particular customer was processed at the corresponding pharmacy location sent from communication device 104, and if so, whether the prescription is now ready for that customer.

In an embodiment, if the prescription is ready, server 110 processes additional rules that determine which pickup location the prescription is routed to within the pharmacy. Further in accordance with this embodiment, once this determination is made, server 110 communicates with pharmacy computer system 112 to notify user 116 and sends one or more notifications to communication device 104 to notify the customer. In this way, system 100 coordinates prescription pickups and their locations between customers and pharmacists.

In an embodiment, once server 110 communicates with pharmacy computing system 112 to determine that a prescription is available for a particular customer at the pharmacy location, server 110 coordinates payment of the prescription. In an embodiment, server 110 notifies communication device 104 that the prescription is ready. Server 110 then optionally sends additional notifications to communication device 104 prompting a user to enter a method of payment. This prompt could include, for example, the cost of the prescription (e.g., post insurance cost to the customer) and/or whether a user wishes to pay this amount using a pre-registered payment method, such as an express payment method, for example. This prompt provides a user the ability to interact with communication device 104 by selecting the preferred payment method and submitting this information to server 110. In an embodiment, if an express payment method is selected, server 110 communicates with pharmacy computer system 112 to verify and/or validate the customers registered payment information. In accordance with such an embodiment, server 112 can connect to the customer's financial institution using information stored on server 110 and/or pharmacy computing system 112 from the customer's completion of an initial registration procedure, for example.

In some embodiments, server 110 optionally sends a prompt, which may be part of the payment prompt or a separate prompt, asking whether the customer has questions for the pharmacist. Server 110 can then appropriately route the customer to the proper location based on the selected payment method and whether the customer has a question. For example, a customer may wish to use an express payment method but could have a question for the pharmacist regarding the dosage, a number of remaining refills, etc. Since express pay counters might not be staffed with pharmacists (i.e., they may only be staffed with cashiers to verify the prescription and customer information) routing the customer to the express payment counter in such a case does not provide the customer with an adequate method to have these questions answered. In this way, system 100 can route the customer to a proper location for prescription pickup based on a payment method and a customer's particular needs.

In accordance with an embodiment, once the transaction is approved by server 110, server 110 sends a notification to communication device 104 indicating that the express payment authorization was successful. This notification could optionally include one or more images representative of the payment authorization, customer identification information, the prescription, the pharmacy location, etc. In an embodiment, the one or more images are implemented as barcodes, such as a barcode or a quick response (QR) code, for example. The barcode can then be displayed on communication device 104 and scanned by pharmacy staff when the customer picks up the prescription at the appropriate pickup location. In an embodiment, a user 116 can scan the barcode displayed on communication device 104 at pharmacy computer terminal 114. Upon scanning the barcode, pharmacy computer terminal 114 communicates with pharmacy computer system 112, which in turn can optionally communicate with server 110 (depending on whether server 110 or pharmacy computer system 112 contains this information) to verify that the customer's information, prescription information, and/or payment authorization information match the information previously generated when the payment was authorized. Once this information is verified by user 116, the prescription transaction can be completed.

In accordance with an embodiment, once the transaction is approved by server 110, server 110 sends a notification to communication device 104 instructing the customer where to pick up the prescription within the pharmacy, at the drive-thru window outside the pharmacy, etc. In various embodiments, these notifications could include text and/or one or more images including these instructions. Images instructing the customer could include, for example, a map of the pharmacy indicating the pickup location, the customer's location, and/or a suggested route for the customer to use to get to the pickup location. In various embodiments, this notification is included in the one or more images representative of the payment authorization or separate from the payment image(s).

In some embodiments, the pharmacy map and/or pickup locations are stored in communication device 104 upon installation of the application. In other embodiments, the pharmacy map and/or pickup locations are accessed by communication device 104 from server 110 and/or pharmacy computing system 112. Similarly, the mapped route, in various embodiments, is calculated by communication device 104, server 110, and/or pharmacy computing system 112.

In some embodiments, the customer's starting location within the mapped route is referenced to the location of a communications device 102 corresponding to the received location beacon. Such embodiments could be particularly useful for smaller pharmacies, or in pharmacies that only have a single communication device 102 positioned at the pharmacy entrance. The mapped route in such embodiments is then displayed in such embodiments from the pharmacy entrance to the appropriate pickup location.

In other embodiments, the customer's location on the mapped route is determined dynamically. For example, as previously discussed, communication device 104 can determine its location as part of a GNSS system, network triangulation, and/or by offloading beacon information to server 110 and/or pharmacy computer system 112. Further in accordance with dynamic location determination embodiments, communication device 104 is configured to receive location beacons from more than one of communication devices 102.1-102.N. In accordance with these embodiments, communication device 104 can obtain its location within the pharmacy via a triangulation of its position between any suitable number of communication devices 102.1-102.N based on the power level received from each communication device 102.

In accordance with various embodiments, server 110 and/or pharmacy communication system 112 is configured to process one or more rules to further determine an appropriate prescription pickup location. In accordance with these embodiments, a priority system can be implemented that overrides the option to route the prescription to the express pickup location. In an embodiment, an override trigger can be set by the payment amount. Financial institutions typically set a maximum monetary amount to transactions that do not require a signature or other form of manual validation (e.g., $50). Since express pay services do not typically provide for this additional level of authentication, prescription costs exceeding this value might not be eligible for express payment. In some embodiments, the notification sent to communications device 104 does not prompt a user to pay with express pay if the prescription cost is over a threshold monetary value. In other embodiments, the notification sent to communications device 104 allows a customer to select the express payment option regardless of the prescription cost, but a second notification is sent to communications device 104 indicating that the express payment has not been successful. In such embodiments, failure to authorize an express payment could result in the notification informing the customer to go to a standard prescription pickup location for payment.

In another embodiment of a rule, a customer having questions for a pharmacist would trigger the notification informing the customer to go to a standard prescription pickup location for payment so that these questions can be answered.

In yet another embodiment of a rule, the type of prescription could control which prescription location the customer is routed to. For example, a customer might be picking up a prescription that is classified as a narcotic, a controlled substance, or a drug that is otherwise subject to enhanced control due to its potential abuse. In some cases, certain prescriptions do not allow other people to pick up prescriptions other than the prescribed customer and/or require a prescription customer to present photo identification. In such a case, server 110 and/or pharmacy communication system 112 is configured to flag this type of prescription and route the customer to a standard prescription pickup counter even if an express payment could otherwise be selected and authorized. In other words, a flagged prescription having a cost that otherwise qualifies for express payment would still route the customer to the standard prescription pickup location.

In further embodiments of a rule, additional restrictions could be placed on specific pickup locations based on additional factors. For example, in an embodiment, a drive-thru or express pickup location may require addition restrictions based on whether a signature is required, the type of prescription, applicable local, state, and/or federal laws, the prescription size and whether the physical size of the drive-thru window and/or sending tube can accommodate the physical size of the prescription, whether a product demonstration is required, the composition of the prescription product (e.g., if it is fragile and/or breakable), etc.

In an embodiment, one or more drive-thru windows utilize the same, or a similar process, regarding express pickup and payment services. For example, a customer may pay for a prescription using express pay via a drive-thru window in the same way a customer would pay for the prescription at an express pay counter inside the pharmacy.

In various embodiments, the rule processing may be made based on any suitable number of inputs and/or parameters, which may be in addition to or in place of other rules previously discussed. Using drive-thru routing as an example, a pharmacy could have one or more drive-thru lanes that are dedicated to express pickup and/or express pay customers. Similar to routing a customer to the express pickup location inside the pharmacy as opposed to the standard counter, embodiments of rules include routing the customer to a preferred drive-thru lane.

In some embodiments, the rules use the location of the customer (e.g., the location of communication device 104) and/or the location of a communication device 102 to determine the prescription pickup location. For example, if other parameters used by one or more rules allow for a customer to pick up a prescription at either an express pickup location or at a drive-thru, various embodiments include the customer being routed to a more appropriate pickup location based on the customer's location. That is, if the customer's location was determined to be within the pharmacy, then the rules could route the prescription to an express pickup location within the pharmacy. On the other hand, if the customer's location was determined to be outside the pharmacy (but still proximate to the pharmacy), then the rules could route the prescription to one or more drive-thru lanes. In this way, embodiments of the present disclosure allow for the efficient routing of prescriptions at various locations associated with a pharmacy based on an identified customer location.

In an embodiment, once the prescription pickup location is determined, user 116 is notified via pharmacy computer terminal 114 of the prescription pickup location. User 116 can then prepare the prescription and/or have the prescription routed to the appropriate location so it is available for the customer. In this way, system 100 allows for an automated coordination of prescription routing within a pharmacy once a customer enters (or is proximate to) the pharmacy with reduced user intervention.

Figure 2:
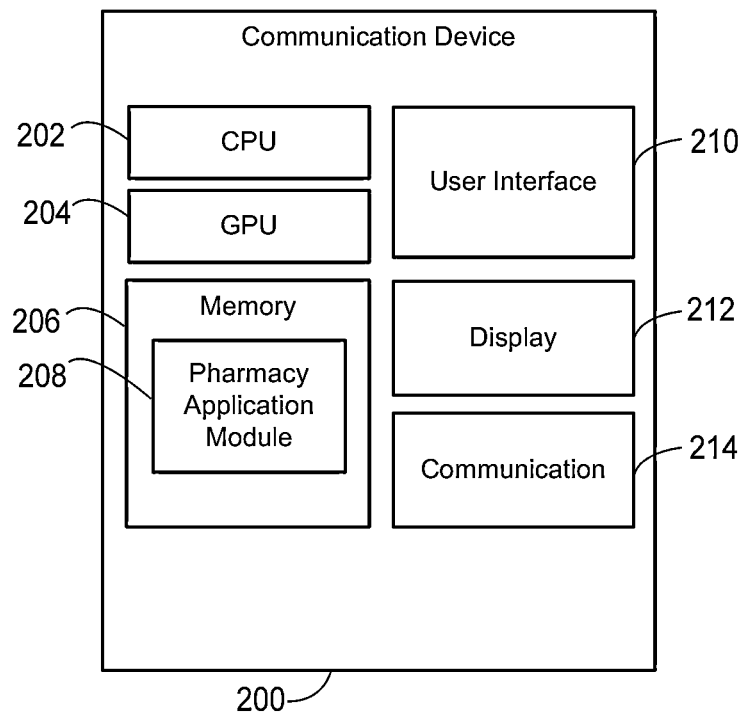
FIG. 2 is a block diagram of an exemplary communication device 200 configured to run a pharmacy application, according to an embodiment.

FIG. 2 is a block diagram of an exemplary communication device configured to run a pharmacy application, according to an embodiment. For ease of explanation, the communication device 200 will be described with reference to the communication device 104 of FIG. 1. However, communication device 200 may be implemented as a communications device other than communication device 104 and/or as part of a system other than system 100.

Communication device 200 includes a central processing unit (CPU) 202, a graphics processing unit (GPU) 204, a memory 206, a user interface 210, a display 212, and a communication unit 214. In an embodiment, communication device 200 is implemented as a user equipment (UE), such as a mobile device, a smartphone, a laptop computer, tablet computer, desktop computer, or any other suitable type of computing device.

Communication unit 214 is configured to enable data communications between communication device 200 and one or more other devices, such as communication devices 102 server 110, and/or pharmacy computing device 112, as shown in FIG. 1. In an embodiment, communication unit 214 is configured to receive data, such as beacon parameters and/or other identifying information, for example, from one or more communications devices. In an embodiment, communication device 200 is configured to send data, including location data and/or customer information, for example, to another device (e.g., a server).

As will be appreciated by those of ordinary skill in the relevant art(s), communication unit 214 may be implemented with any combination of suitable hardware and/or software to enable these functions. For example, communication unit 214 may be implemented with any number of wired and/or wireless transceivers, network interfaces, physical layers (PHY), etc. In embodiments in which communication device 200 is a mobile device, communication unit 214 optionally enables communications between communication device 200 and one or more networks, such as network 108, for example, as shown in FIG. 1.

In various embodiments, communication unit 214 is configured to measure the strength of signals received from other communication devices and to provide these measurements to CPU 202. For example, in embodiments in which communication device 200 is implemented as a mobile device, communication unit 214 may be configured to measure the signal strength of signals received from one or more location beacon transmissions. Alternatively or additionally, communication unit 214 may be configured to measure signal strengths of signals received from one or more access points. In this way, communication unit 214 may provide CPU 202 a way of determining a location of communication device 200.

User interface 210 is configured to allow a user to interact with communication device 200. For example, user interface 210 may include a user-input device such as an interactive portion of display 212 (e.g., a "soft" keyboard displayed on display 212), an external hardware keyboard configured to communicate with communication device 200 via a wired or a wireless connection (e.g., a Bluetooth keyboard), an external mouse, or any other suitable user-input device.

CPU 202 and/or GPU 204 are configured to communicate with memory 206 to store to and read data from memory 206. In accordance with various embodiments, memory 206 is a computer-readable non-transitory storage device that may include any combination of volatile (e.g., a random access memory (RAM), or a non-volatile memory (e.g., battery-backed RAM, FLASH, etc.). Memory 206 is configured to store instructions executable on CPU 202 and/or GPU 204. These instructions may include machine readable instructions that, when executed by CPU 204 and/or GPU 204, cause CPU 202 and/or GPU 204 to perform various acts. Memory 206 is configured to store other information, for example, such as pharmacy store locations, a list of communication device identifiers and their corresponding store locations, customer information, etc.

Pharmacy application module 208 is a portion of memory 206 configured to store instructions, that when executed by CPU 202 and/or GPU 204, cause CPU 202 and/or GPU 204 to enable user interface 210 to collect user input and to display feedback and/or notifications to a user in accordance with one or more applications and/or programs. For example, executable instructions stored in pharmacy application module 208 may enable user interface 210 to display one or more prompts and/or notifications to a user and/or to accept user input, which could include selecting payment methods, for example. In an embodiment, instructions stored in pharmacy application module 208 enable a user to enter suitable data to obtain a prescription pickup location within a pharmacy. In various embodiments, information, such as pharmacy store locations, a list of communications device identifiers and corresponding store locations, customer information, etc., could be stored as part of pharmacy application module 208 or elsewhere within memory 206.

In various embodiments, the information and/or instructions stored in pharmacy application module 208 are setup upon the initial installation of a pharmacy application. In some embodiments, the pharmacy application can be installed in addition to an operating system implemented by a communication device, such communication devices 104 and 200, for example, as shown in FIGS. 1 and 2. For example, a user could download and install the pharmacy application from an application store via communication unit 214 using user interface 210. Application stores could include, for example, Apple Inc.'s App Store, Google Inc.'s Google Play, Microsoft Inc.'s Windows Phone Store, etc., depending on the applicable operating system implemented by communication device 200.

In other embodiments, the information and/or instructions stored in pharmacy application module 208 are integrated as a part of the operating system implemented by a communication device, such communication devices 104 and 200, for example, as shown in FIGS. 1 and 2. For example, a user could setup the pharmacy application via an initial setup procedure upon initialization of the communication device, as part of setting up a new user account on the communication device, etc.

In various embodiments, pharmacy application module 208 enables communications device 200 to facilitate sending and/or receiving data to and/or from another device, such as communication devices 102, server 110, and/or pharmacy computing device 112, for example, via communication unit 214. For example, pharmacy application module 208 could include instructions that enable CPU 202 to determine that communication device 200 is within the proximity of one or more location beacons based on measurements performed by communications unit 214. In an embodiment, the instructions included in pharmacy application module 208 enable CPU 204 to perform contextual actions in response to the detection of location beacons received by communications unit 214 without user intervention. For example, as previously discussed with reference to FIG. 1, when one or more location beacons are received, pharmacy application module 208 could include instructions that enable CPU 202 to cause communication unit 214 to send data to another device, such as server 110, for example, as shown in FIG. 1.

Figure 3A:
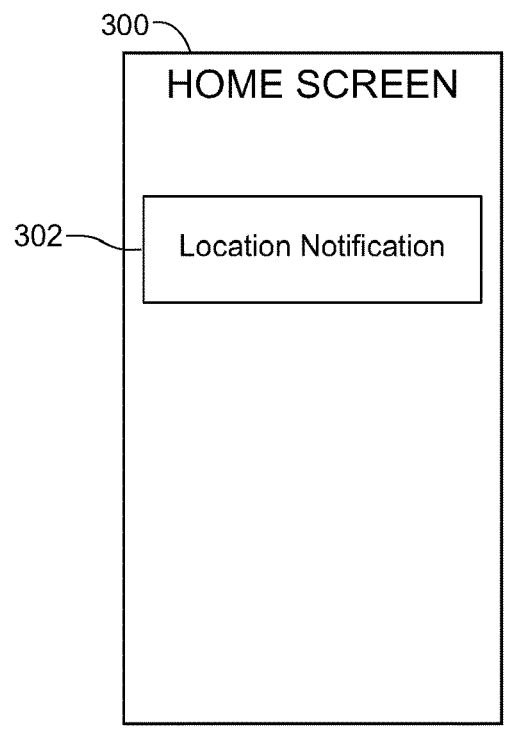
FIG. 3A illustrates an exemplary communication device home screen 300, according to an embodiment.

FIG. 3A illustrates an exemplary communication device home screen 300, according to an embodiment. In various embodiments, home screen 300 is displayed on a communication device, such as communication device 104 or communication device 200, as shown in FIGS. 1 and 2, respectively. In accordance with such embodiment, home screen 300 is displayed as part of a communication device display, such as display 212, as shown in FIG. 2.

Home screen 300 is an example of a mobile device home screen. For example, home screen 300 could be displayed as a "default" screen when no applications are otherwise running on the communications device. In an embodiment, home screen 300 is a "lock screen" of a mobile phone. Lock screens are typically displayed when a user locks the phone when a user enters a lock screen mode (e.g., by pressing a physical button) or the phone may revert to the lock screen when the phone is inactive for a period of time. The lock screen prevents a user from using a portion of the mobile device functionality. For example, a lock screen might prevent a phone in a user's pocket from accidentally sending text messages or phone calls.

Although lock screens typically limit the functionality of the device, it may be desirable for certain applications to provide a user with some functionality via the lock screen. For example, if the phone is used to play music, a lock screen overlay could allow a user to change tracks, pause a track, or adjust the volume level without unlocking the phone. In accordance with some embodiments, location notification 302 is displayed as part of a home screen and/or lock screen, as shown in FIG. 3A.

Although location notification 302 is displayed as part of home screen 300 in FIG. 3A, other embodiments include location notification 302 being displayed as part of a notification system separate from home screen 300. For example, some mobile phone operating systems implement a universal "pull-down" notification system where all incoming notifications are displayed. In these notification systems, new notifications are initially previewed in a notifications bar at the top of the phone display, and a user can pull down (e.g., by using a swiping gesture) the notification bar to access the details of any received notifications. In an embodiment, location notification 302 is displayed as part of a notification bar type notification.

As previously discussed with reference to FIG. 1, in accordance with an embodiment, a communication device that has installed the pharmacy application is configured to detect its proximity to other communication devices by receiving one or more broadcasted location beacons. Location notification 302 is an example of a notification displayed at a communication device that has detected its proximity to a location beacon, and, based on the beacon parameters broadcasted over the beacon, determined the beacon matches a pharmacy location.

Figure 3B:
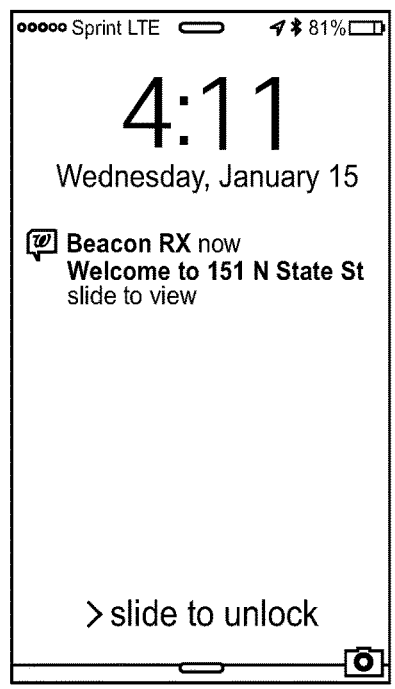
FIG. 3B illustrates an image of an exemplary communication device home screen, according to an embodiment.

FIG. 3B illustrates an image of an exemplary communication device home screen, according to an embodiment. FIG. 3B is an example image of a lock screen displaying the location notification. Using the previous example discussed with reference to FIG. 3A, the pharmacy location determined from the beacon parameters is associated with a street address of the pharmacy corresponding to "151 N. State St." As shown in FIG. 3B, various embodiments include graphical representations of the application that triggered this notification and/or a description of the type of trigger notification (i.e., "Beacon RX"). Again, embodiments include displaying the location notification upon detection of a beacon transmission without intervention from the user.

Figure 3C:
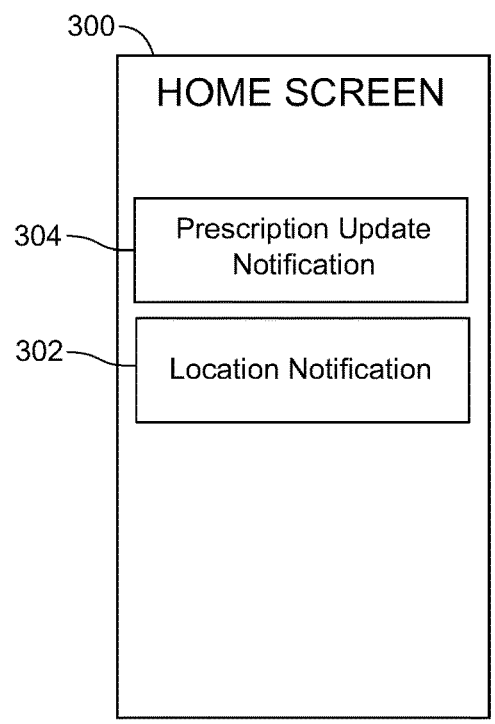
FIG. 3C illustrates an exemplary communication device home screen 300, according to an embodiment.

FIG. 3C illustrates an exemplary communication device home screen 300, according to an embodiment. As previously discussed with reference to FIG. 1, in accordance with an embodiment, once a communication device has determined the pharmacy location, the customer's contact information and this location information (or a location identifier) can be sent to a server via an API services call so a determination can be made whether a customer's prescription is ready at that location. Prescription update notification 304 is an example of a notification displayed on a communication device once the communications device determines a pharmacy location and receives a notification that the prescription is ready at that pharmacy location. Although FIG. 3C illustrates the prescription update notification 304 being displayed above location notification 302, various embodiments include prescription update notification 304 displayed at any suitable location within home screen 300, or as part of another notification system (e.g., a notification bar) as previously discussed.

Figure 3D:
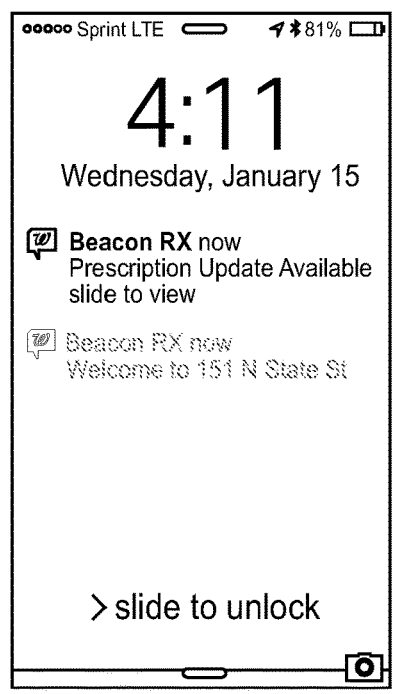
FIG. 3D illustrates an image of an exemplary communication device home screen, according to an embodiment.

FIG. 3D illustrates an image of an exemplary communication device home screen, according to an embodiment. FIG. 3D is an example image of a lock screen displaying the prescription update notification. Using the previous example discussed with reference to FIG. 3C, the notification that a customer has a prescription available at the pharmacy location is displayed as "prescription update available." As shown in FIG. 3D, various embodiments include graphical representations of the application that triggered this notification and/or a description of the type of trigger notification (i.e., "Beacon RX"). In an embodiment, a user may then continue to obtain details regarding the prescription cost, payment, and prescription pickup location by performing one or more gestures such as tapping and/or swiping the prescription update notification and/or unlocking the device.

Figure 4A:
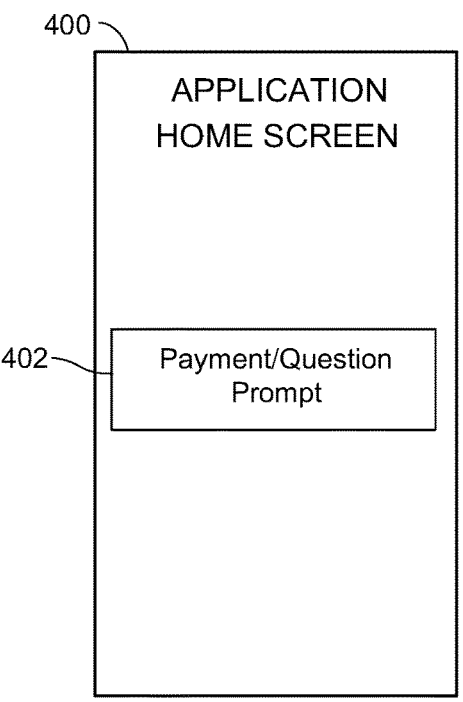
FIG. 4A illustrates an exemplary communication device application home screen 400, according to an embodiment.

FIG. 4A illustrates an exemplary application home screen, according to an embodiment. In various embodiments, application home screen 400 is displayed on a communication device, such as communication device 104 or communication device 200, as shown in FIGS. 1 and 2, respectively. In accordance with such embodiment, application home screen 400 is displayed as part of a communication device display, such as display 212, as shown in FIG. 2. In an embodiment, application home screen 400 is displayed once a user interacts with the notifications displayed in FIG. 3D. For example, once the prescription update notification 304 is displayed, a user can tap the notification and/or perform one or more gestures to unlock the phone, resulting in the display of application home screen 400.

In an embodiment, application home screen 400 is implemented as the main screen for a pharmacy application running on a communication device. In accordance with such an embodiment, application home screen 400 could include various interactive buttons, tiles, etc., to allow a user to interact with the pharmacy application. For example, a pharmacy application could allow a user to lookup her prescriptions, pharmacy locations, etc. In accordance with an embodiment, application home screen 400 displays a payment/question prompt notification 402 on application home screen if the pharmacy application is launched and a prescription is ready at the customer's pharmacy location. Payment/question prompt notification 402 provides a user with the ability to select a method of payment for the prescription. Alternatively or additionally, payment/question prompt notification 402 allows a user to select an option to ask a pharmacist questions regarding the prescription.

Figure 4B:
FIG. 4B illustrates an image of an exemplary communication device application home screen, according to an embodiment.

FIG. 4B illustrates an image of an application home screen, according to an embodiment. FIG. 4B is an example image of an application home screen displaying the payment and/or question prompt notification. Using the previous example discussed with reference to FIG. 4A, the payment and/or question prompt notification provides separate virtual switch-type buttons that allow a user to select the payment type and indicate whether he has questions for a pharmacist. In an embodiment, once a user selects these options, the "submit" box can be selected with an appropriate gesture and this information submitted to a server and/or a pharmacy computer system, as previously discussed with reference to FIG. 1. Further in accordance with an embodiment, a user can cancel the transaction by selecting the "cancel" button accordingly.

As shown in FIG. 4B, the pharmacy application tiles behind the payment and/or question prompt notification allow a user to select various functions via the pharmacy application. Although FIG. 4B illustrates the image of the payment and/or question prompt notification using virtual switches, any suitable input system can be implemented to allow a user to select the desired options. For example, the payment and/or question prompt notification could include checkboxes, radio buttons, etc.

Figure 4C:
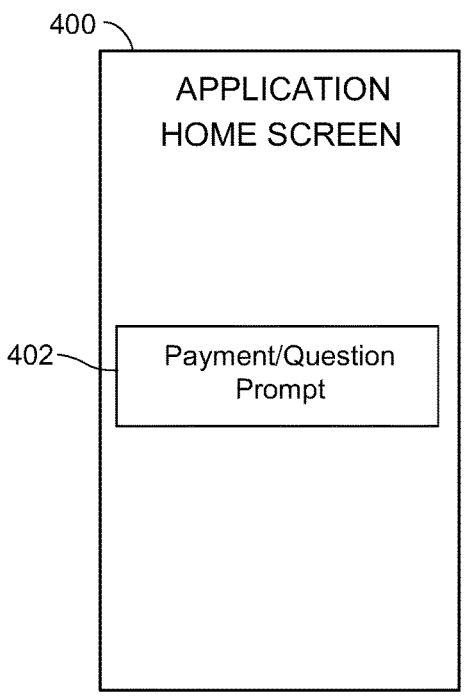
FIG. 4C illustrates an exemplary communication device application home screen 400, according to an embodiment.

FIG. 4C illustrates an application home screen 400, according to an embodiment. In accordance with various embodiments, application home screen 400 includes pickup location map notification 404 and/or payment barcode/error indication 406. In an embodiment, pickup location map notification 404 and/or payment barcode/error indication 406 are displayed on application home screen 400 once a payment is authorized (or declined) and the prescription pickup location and/or the customer's location within the pharmacy are determined. For example, using the example input shown in FIG. 4B, a user may submit the options shown in FIG. 4B, successfully authorize an express payment, and not have questions for the pharmacist. In this case, payment barcode/error indication 406 could include a generated payment barcode (e.g., via a server and/or pharmacist computer system as previously discussed with reference to FIG. 1) including payment and/or other verification information. This payment barcode can later be scanned by a pharmacy staff member to complete the transaction.

However, if the express pay request is rejected, for example, due to an amount exceeding a threshold monetary value, then payment barcode/error indication 406 can include an error message indicating this. Various embodiments include an error message further detailing reasons why the express payment was declined, an indication that the prescription is not eligible for express pickup and/or payment, etc.

Once the prescription pickup location is determined (e.g., via a server and/or pharmacist computer system as previously discussed with reference to FIG. 1), pickup location map 404 includes a map and/or route notifying a customer where to go in the pharmacy corresponding to that pickup location. Although FIG. 4C illustrates pickup location map 404 displayed above payment barcode 406, various embodiments display pickup location map 404 and/or payment barcode 406 at any suitable location within home screen 400, or as part of another notification system (e.g., a notification bar) as previously discussed.

Figure 4D:
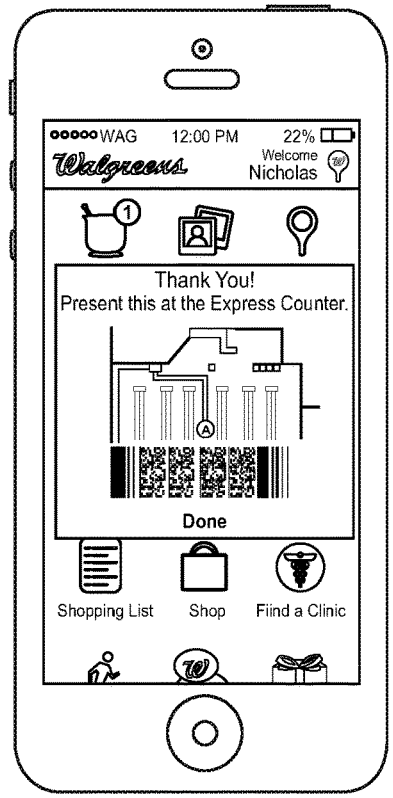
FIG. 4D illustrates an image of an exemplary communication device application home screen, according to an embodiment.

FIG. 4D illustrates an image of an exemplary application home screen, according to an embodiment. FIG. 4D is an example image of an application home screen displaying the pickup location map and the payment barcode. Using the previous example discussed with reference to FIG. 4C, the pickup location map informs the customer that the prescription is at the express counter, and also displays a route for the customer to follow to get to the express counter. In addition, the example image illustrates a barcode that can be scanned by the pharmacy staff once the customer arrives at the express counter to complete the transaction.

Figure 5:
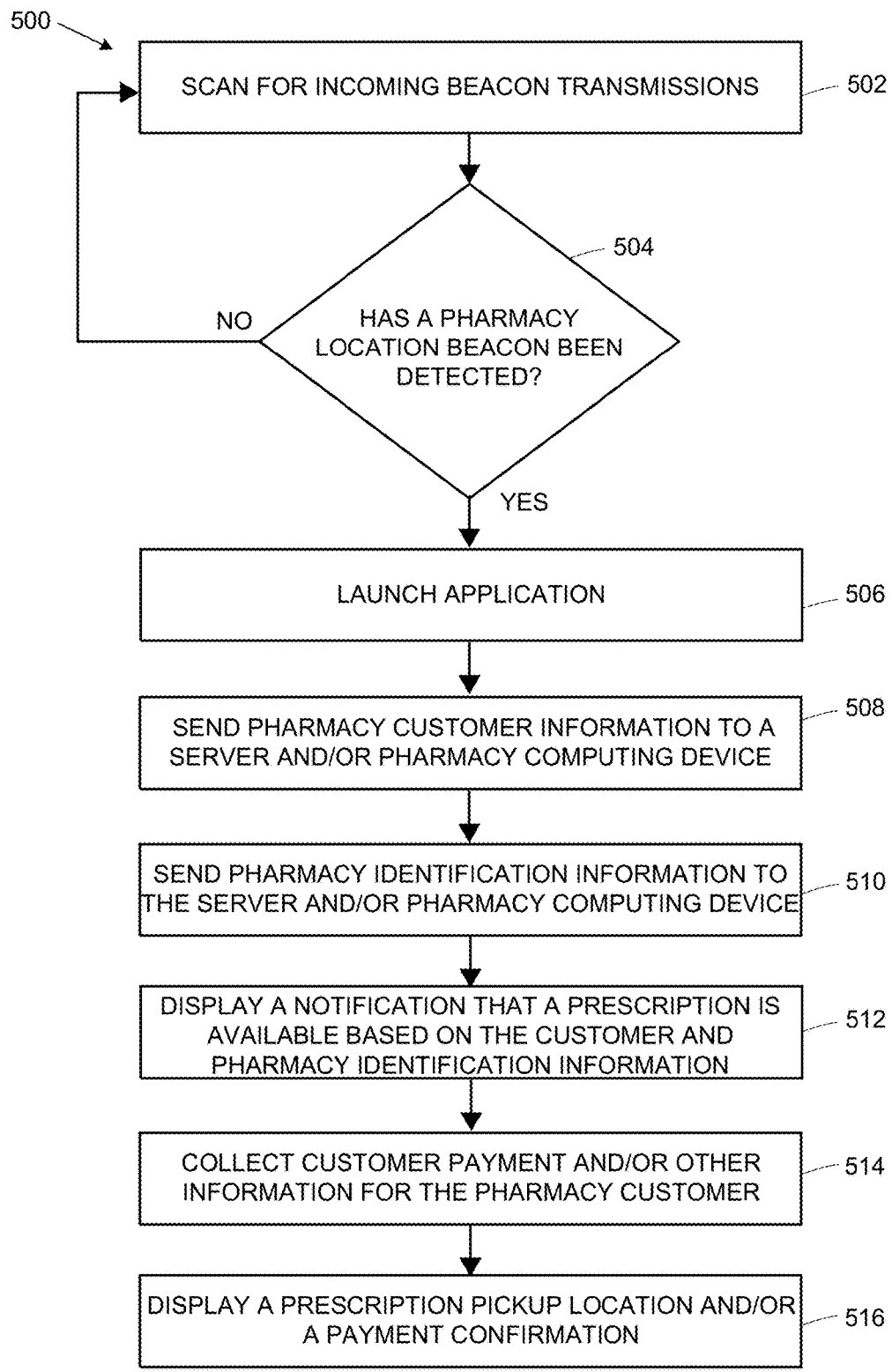
FIG. 5 is a flow chart showing an exemplary method for displaying prescription pickup location information and payment confirmation information to a pharmacy customer, according to an embodiment.

FIG. 5 is a flow chart showing an exemplary method for displaying prescription pickup location information to a pharmacy customer, according to an embodiment. In an embodiment, method 500 is implemented by a communication device, such as communication device 104 and communication device 200, as shown in FIGS. 1 and 2. Various embodiments of the flow chart shown in FIG. 5 could include a the blocks associated with the execution of an installed pharmacy application on a communication device, such as communication device 104 and communication device 200, as shown in FIGS. 1 and 2. Again, these embodiments could include the execution of applications that are integrated as a part of the operating system installed on the communication device or installed as an application in addition to the operating system.

At block 502, a communication device scans for incoming beacon transmissions. The communication device includes, for example, communication device 104 or communication device 200, as shown in FIGS. 1 and 2, respectively, in some embodiments. The beacons could be transmitted, for example, by communications devices 102, as shown in FIG. 1, in some embodiments. The beacon transmissions include a beacon device identifier and/or a calibrated transmitted power measurement, in an embodiment.

At block 504, the communication device determines whether a pharmacy location beacon been detected. For example, block 504 includes the communication device referencing a beacon identifier to a list of pharmacy beacon identifiers to determine if the beacon identifier corresponds to a known pharmacy location, in an embodiment. To provide another example, block 504 includes the communication device sending the beacon identifier to another device, such as a server and/or a pharmacy computing device, for example, and receiving a determination made by the server and/or the pharmacy computing device that the beacon corresponds to a pharmacy location beacon, in an embodiment. If the received beacon corresponds to a pharmacy location beacon, then method 500 continues to block 506. On the other hand, if the beacon does not correspond to a known pharmacy location beacon, method 500 reverts back to block 502 and continues to scan incoming beacon transmissions.

At block 506, the communication device launches an installed pharmacy application. For example, block 506 includes the communication device launching the application as part of one or more background processes and without user intervention, in an embodiment. To provide another example, block 506 includes the communication device displaying a notification that the beacon was detected, such as the location notification as shown in FIGS. 3A-B, in an embodiment.

At block 508, the application causes the communication device to send pharmacy customer information to a server and/or a pharmacy computing device. For example, block 508 includes the application sending a customer's date of birth, last name, and/or phone number so the customer can be properly identified, in an embodiment. In an embodiment, the customer identification information is automatically sent upon the launch of the application without user intervention.

At block 510, the application causes the communication device to send pharmacy information to a server and/or a pharmacy computing device. For example, block 510 includes the application sending beacon identification information, such as a UUID that is broadcasted in the beacon so the pharmacy location can be properly identified, in an embodiment. In an embodiment, the pharmacy information is automatically sent upon the launch of the application without user intervention.

At block 512, the communication displays a notification that a prescription is available based on the customer information and the pharmacy information. For example, block 512 could include the communication device receiving a notification sent from the server and/or the pharmacy computing device that the prescription is available at the pharmacy location and display this notification, in an embodiment. In an embodiment, the notification received from the server and/or the pharmacy computing device is a push notification. The notification could include for example, the notifications as shown in FIGS. 3C-D.

At block 514, the communication device collects payment and/or other information for the pharmacy customer. For example, block 514 could include the communication device displaying one or more prompts that allow a user to select a method of payment and/or to indicate that the customer has questions for the pharmacist, in an embodiment. To provide another example, block 514 could include server 110 and/or pharmacy computing system 112 receiving payment information and/or other information corresponding to the pharmacy customer from the communication device (e.g., entered by the customer) and/or from another device, such as another database, server, etc., in an embodiment. The prompts could include for example, the payment and/or question prompts as shown in FIGS. 4A-B.

At block 516, the communication device displays a prescription pickup location and/or a payment confirmation. In an embodiment, block 516 includes the server and/or the pharmacy computing device making a determination of a prescription location and whether the payment is authorized based on the payment information and/or other information submitted by the pharmacy customer. In an embodiment, block 516 includes the server and/or the pharmacy computing device making a determination of the prescription pickup location based on additional information, such as a prescription type, for example. Once the determination is made, block 516 includes the communication device displaying a pickup location within the pharmacy and/or a confirmation of whether the payment was successful to the customer. In an embodiment, the displayed pickup location and/or payment confirmation could include, for example, the pickup location map and/or payment barcode/error indication as shown in FIGS. 4C-D.

Embodiments of the present disclosure relate to one or more of the following clauses.

In an first embodiment, a method is performed by a first communication device includes detecting a proximity of the first communication device to a pharmacy location, sending prescription customer identification information to a pharmacy computing device, sending pharmacy identification information to the pharmacy computing device, displaying a notification that a prescription is available for the prescription customer at the pharmacy based on a determination made by the pharmacy computing device using the prescription customer identification and the pharmacy identification information, and displaying a prescription pickup location associated with the pharmacy based on the determination made by the pharmacy computing device.

Variations of the first and other embodiments include the detecting including detecting the proximity of the first communication device to the pharmacy location by receiving a signal transmitted by a second communications device associated with the pharmacy location.

Variations of the first and other embodiments additionally include the act of receiving including receiving the signal transmitted by the second communications device in accordance with a personal area network (PAN) communication protocol.

Variations of the first and other embodiments also include the act of displaying including displaying the notification received from the pharmacy computing device as a push notification.

Variations of the first and other embodiments also include determining the prescription pickup location as a first location associated with the pharmacy based when a payment transaction sent by the first communication device is successful, and determining the prescription pickup location as a second location when the payment transaction is unsuccessful.

Variations of the first and other embodiments also include the act of displaying the prescription location displaying a map of the pharmacy including an indication of the first or the second location.

Variations of the first and other embodiments also include the act of displaying the prescription location including displaying the map of the pharmacy including a route between a location of the first communication device and the first or the second location.

Variations of the first and other embodiments also include displaying, by the first communication device, a prompt requesting whether questions need to be submitted to a pharmacist.

In a second embodiment, a non-transitory computer readable media having instructions stored thereon in a first communications device is executed by a processor to cause the processor to detect a proximity of the communication device to a pharmacy location, send pharmacy identification information to the pharmacy computing device, send customer identification information to the pharmacy computing device, display a notification that a prescription is available for the prescription customer at the pharmacy based on a determination made by the pharmacy computing device using the pharmacy identification information and the customer identification information, and display a prescription pickup location associated with the pharmacy based on the determination made by the pharmacy computing device.

Variations of the second and other embodiments also include the instructions causing the processor to detect the proximity of the first communication device to the pharmacy location by receiving a signal transmitted by a second communications device positioned at the pharmacy location.

Variations of the second and other embodiments also include the instructions causing the processor to receive the signal transmitted by the second communications device in accordance with a personal area network (PAN) communication protocol.

Variations of the second and other embodiments also include the instructions causing the processor to display the notification received from the pharmacy computing device as a push notification.

Variations of the second and other embodiments also include the instructions causing the processor to determine the prescription pickup location as a first location associated with the pharmacy when a payment transaction sent by the first communication device is successful, and to determine the prescription pickup location as a second location when the payment transaction is unsuccessful.

Variations of the second and other embodiments also include the instructions causing the processor to display a map image of the first or the second location associated with the pharmacy.

Variations of the second and other embodiments also include the instructions causing the processor to display the map image including a route between a location of the first communication device and the first or the second location associated with the pharmacy.

Variations of the second and other embodiments also include the instructions causing the processor to display a prompt requesting whether questions need to be submitted to a pharmacist.

In a third embodiment, a method is performed by a first communication device and includes displaying a first notification that the first communication device has entered a pharmacy based on detecting a proximity of the first communication device to a second communication device associated with the pharmacy, sending information identifying the prescription customer and the pharmacy location to a pharmacy computing device, displaying a second notification based on an indication received from the pharmacy computing device that a prescription is ready at a prescription pickup location associated with the pharmacy based on the information, and displaying a map of the prescription pickup location.

Variations of the third and other embodiments also include displaying or more of (1) a prompt requesting a method of payment for the prescription, and (2) an image representative of payment for the prescription.

Variations of the third and other embodiments also include detecting the proximity of the first communication device to the second communication device associated with the pharmacy the pharmacy location by receiving a signal transmitted by the second communications device positioned at the pharmacy location.

Variations of the third and other embodiments also include the act of receiving the signal including receiving the signal transmitted by the second communications device in accordance with a personal area network (PAN) communication protocol.

Variations of the third and other embodiments also include determining the prescription pickup location as a first location associated with the pharmacy when a payment transaction sent by the first communication device is successful, and determining the prescription pickup location as a second location when the payment transaction is unsuccessful.

Variations of the third and other embodiments also include the act of displaying the prescription location including displaying the map image including a route between a location of the first communication device and the first or the second location associated with the pharmacy.

As used herein, the term "pharmacy" may include, for example, a single outlet or a plurality of outlets affiliated with one or more entities that are licensed to dispense prescribed pharmaceutical products such as drugs, medicaments, durable medical equipment, etc. The one or more entities may be located, for example, in geographic locations separate from one another, in different areas of the same city, or in different states, countries, etc. The pharmacy outlets may include, for example, one or more of a conventional retail store, space within a location operated by another commercial or not-for-profit entity (e.g., within a discount store, hospital, school, nursing home, etc.), an outlet in proximity with a warehouse or distribution center, a call-in pharmacy, a long-term care pharmacy, a workplace/on-site pharmacy, a specialty pharmacy, etc. The pharmacy may be commercial or not-for-profit, and may provide or vend other products in addition to the prescribed pharmaceutical products.

As used herein, the term "pharmacy computing system" may include a computing system that is owned and/or operated by a pharmacy to aid pharmacy employees and representatives to fill and dispense prescribed pharmaceutical products and other products. A pharmacy computing system may include at least one computing device, database, display device, and user input interface device. Typically, each outlet of a pharmacy may have a local instance of (or local access to) a pharmacy computing system. In some embodiments, local instances of a pharmacy computing system may be networked.

As used herein, the terms "customer", "pharmacy customer", or "patient" are interchangeable and may refer to a person who has been prescribed one or more pharmaceutical products such as drugs, medicaments, durable medical equipment, or the like. Additionally or alternatively, the interchangeable terms "pharmacy customer", "customer", or "patient" may refer to such person's representative. The representative may be, for example, a patient's caregiver or another suitable person who may interact with a pharmacy employee or pharmacy representative on behalf of a patient. Such interaction may occur in conjunction with a filling of or payment for a prescription order for the patient, including a refill order.

As used herein, the terms "pharmacy employee," "pharmacy representative," or "pharmacy technician" are interchangeable and may refer to a licensed pharmacist or a non-licensed pharmacy employee or pharmacy representative.

It will be appreciated that various embodiments of the system and methods described herein allow, among other advantages, an advance identification of a customer to be sent to a pharmacy technician when the customer arrives at a pharmacy to pick up an order (e.g., a prescription refill). Thus, the pharmacy technician may obtain the customer's previously prepared pharmacy order and bring the previously prepared pharmacy order to a pharmacy pick-up area before or during the customer's check-out/payment process for the refill, and/or before or during one or more other aspects of a transaction for the previously prepared pharmacy order. As a result, the previously prepared pharmacy order may be handed to the customer as soon as the check-out/payment process is complete, avoiding unnecessary delays or wait times which would occur if the pharmacy technician only began to obtain the customer's previously prepared pharmacy order after the customer had already approached the pharmacy pick-up area and identified himself or herself.

Although the foregoing text sets forth a detailed description of numerous different embodiments, it should be understood that the detailed description is to be construed as exemplary only and does not describe every possible embodiment because describing every possible embodiment would be impractical, if not impossible. In light of the foregoing text, one of ordinary skill in the art will recognize that numerous alternative embodiments could be implemented, using either current technology or technology developed after the filing date of this patent application.

What is claimed is:

1. A method for providing a prescription pickup location for a prescription order, comprising:

receiving, by a mobile communication device at a pharmacy, one or more transmitted beacon parameters that are transmitted from a beacon communication device that is positioned at a predetermined pharmacy location at the pharmacy, the beacon parameters including a calibrated receive power value;

detecting, by the mobile communication device, a proximity of the mobile communication device to the predetermined pharmacy location when the mobile communication device is within a threshold distance of the beacon communication device based upon an analysis of the one or more transmitted beacon parameters;

in response to detecting the proximity of the mobile communication device to the predetermined pharmacy location, triggering an execution of an application installed on the mobile communication device to cause the mobile communication device to transmit (i) prescription customer identification information and (ii) the proximity to a server at the pharmacy;

when the server determines (i) that the mobile communication device is positioned at the predetermined pharmacy location based upon the proximity, (ii) that the prescription is available for the prescription customer at the pharmacy based upon a correlation of the prescription customer identification information to stored prescription information, and (iii) a prescription pickup location from among several possible prescription pickup locations based upon an application of one or more rules that utilize information associated with the prescription order and the prescription customer, receiving, in the mobile communication device, a notification that a prescription is available for the prescription customer at the determined prescription pickup location; and in response to receiving the notification, displaying, on the mobile communication device, (i) an indication that the prescription is available for the prescription customer at the pharmacy, and (ii) the prescription pickup location.

2. The method of claim 1, wherein the act of detecting the proximity of the mobile communication device to the predetermined pharmacy location comprises:

detecting the proximity of the mobile communication device to the predetermined pharmacy location by determining a received signal strength value of a signal used by the beacon communication device to transmit the one or more transmitted beacon parameters, and comparing the received signal strength value to the calibrated receive power value such that, when the received signal strength value is greater than the calibrated receive power value, the proximity of the mobile communication device to the predetermined pharmacy location is detected.

3. The method of claim 1, wherein the act of receiving the one or more transmitted beacon parameters comprises:

receiving the one or more transmitted beacon parameters from the beacon communication device in accordance with a personal area network (PAN) communication protocol.

4. The method of claim 1, wherein the notification is a push notification.

5. The method of claim 1, further comprising:

displaying the prescription pickup location as a first location when a payment transaction initiated by the mobile communication device is successful; and displaying the prescription pickup location as a second location when the payment transaction is unsuccessful.

6. The method of claim 5, wherein the act of displaying the prescription pickup location comprises:

displaying a map of the pharmacy including an indication of the first location or the second location.

7. The method of claim 6, wherein the act of displaying the prescription pickup location further comprises:

displaying the map of the pharmacy including a route between a location of the mobile communication device and the first location or the second location.

8. The method of claim 1, further comprising:

displaying, by the mobile communication device, a prompt requesting whether questions need to be submitted to a pharmacist, wherein the information associated with the prescription order includes user input entered via the mobile communication device in response to the prompt.

9. The method of claim 1, wherein the information associated with the prescription order includes one of more of:

user input received from the mobile communication device;

payment information associated with the prescription order;

a type of prescription drug associated with the prescription order; and a location of the mobile communication device.

10. A non-transitory computer readable media having instructions stored thereon in a mobile communication device for providing a prescription pickup location for a prescription order, that when executed by a processor cause the mobile communication device to:

receive one or more transmitted beacon parameters that are transmitted from a beacon communication device that is positioned at a predetermined pharmacy location at a pharmacy, wherein the one or more transmitted beacon parameters include a calibrated receive power value;

analyze the one or more transmitted beacon parameters to detect a proximity of the mobile communication device to the predetermined pharmacy location when the mobile communication device is within a threshold distance of the beacon communication device;

in response to detecting the proximity of the mobile communication device to the predetermined pharmacy location, trigger an execution of an application installed on the mobile communication device to cause the mobile communication device to transmit prescription customer identification information, and the proximity, to a server at the pharmacy;

when the server determines (i) that the mobile communication device is positioned at the predetermined pharmacy location based upon the proximity, (ii) that the prescription is available for the prescription customer at the pharmacy based upon a correlation of the prescription customer identification to stored prescription information, and (ii) a prescription pickup location from among several possible prescription pickup locations based upon an application of one or more rules that utilize information associated with the prescription order and the prescription customer, receiving, in the mobile communication device, a notification transmitted by the server that a prescription is available for the prescription customer at the determined prescription pickup location; and in response to receiving the notification, to display (i) an indication that the prescription is available for the prescription customer at the pharmacy and (ii) the prescription pickup location.

11. The non-transitory computer readable media of claim 10, wherein the instructions, when executed by the processor, further cause the processor to detect the proximity of the mobile communication device to the predetermined pharmacy location by determining a received signal strength value of a signal used by the beacon communication device to transmit the one or more transmitted beacon parameters and comparing the received signal strength value to the calibrated receive power value such that, when the received signal strength value is greater than the calibrated receive power value, the proximity of the mobile communication device to the predetermined pharmacy location is detected.

12. The non-transitory computer readable media of claim 10, wherein the instructions, when executed by the processor, further cause the mobile communication device to receive the one or more transmitted beacon parameters from the beacon communication device in accordance with a personal area network (PAN) communication protocol.

13. The non-transitory computer readable media of claim 10, wherein the notification is a push notification.

14. The non-transitory computer readable media of claim 10, wherein the instructions, when executed by the processor, further cause the mobile communication device to:
display the prescription pickup location as a first location when a payment transaction initiated by the mobile communication device is successful; and
display the prescription pickup location as a second location when the payment transaction is unsuccessful.

15. The non-transitory computer readable media of claim 14, wherein the instructions, when executed by the processor, further cause the mobile communication device to display a map image of the first location or the second location.

16. The non-transitory computer readable media of claim 15, wherein the instructions, when executed by the processor, further cause the mobile communication device to display the map image including a route between a location of the mobile communication device and the first location or the second location.

17. The non-transitory computer readable media of claim 10, wherein the instructions, when executed by the processor, further cause the mobile communication device to display a prompt requesting whether questions need to be submitted to a pharmacist,
wherein the information associated with the prescription order includes user input entered via the mobile communication device in response to the prompt.

18. The non-transitory computer readable media of claim 10, wherein the information associated with the prescription order includes one of more of:
user input received from the mobile communication device;
payment information associated with the prescription order;
a type of prescription drug associated with the prescription order; and
a location of the mobile communication device.

19. A method for providing a prescription pickup location for a prescription order, comprising:
displaying, by a mobile communication device, a first indication that the mobile communication device has entered a pharmacy based on a detection of a proximity of the mobile communication device to a beacon communication device that is positioned at a predetermined pharmacy location at the pharmacy when the mobile communication device is within a threshold distance of the beacon communication device;
in response to detecting the proximity of the mobile communication device to the predetermined pharmacy location, triggering an execution of an application installed on the mobile communication device to cause the mobile communication device to transmit information identifying the prescription customer and the predetermined pharmacy location to a server at the pharmacy,
when the server determines (i) that the mobile communication device is positioned at the predetermined pharmacy location based upon the proximity, (ii) that the prescription is ready at the pharmacy based upon a correlation of the information identifying the prescription customer and the pharmacy to stored prescription information, and (iii) a prescription pickup location from among several possible prescription pickup locations based upon an application of one or more rules that utilize information associated with the prescription order and the prescription customer, receiving, in the mobile communication device, a notification that a prescription is available for the prescription customer at the determined prescription pickup location; and
in response to receiving the notification, displaying, by the mobile communication device (i) a second indication that the prescription is available for the prescription customer at the prescription pickup location, and (ii) a map of the pharmacy including the prescription pickup location at the pharmacy.

20. The method of claim 19, further comprising:
displaying, at the mobile communication device, one or more of the following:
a prompt requesting a method of payment for the prescription; and
an image representative of payment for the prescription.

21. The method of claim 19, further comprising:
detecting the proximity of the mobile communication device to the beacon communication device by (i) determining a received signal strength value of a signal transmitted by the beacon communication device, (ii) receiving a calibrated receive power value encoded into the signal, and (iii) comparing the received signal strength value to the calibrated receive power value such that, when the received signal strength value is greater than the calibrated receive power value, the proximity of the mobile communication device to the beacon communication device is detected.

22. The method of claim 21, wherein the one or more transmitted beacon parameters transmitted by the beacon communication device are received by the mobile communication device in accordance with a personal area network (PAN) communication protocol.

23. The method of claim 21, further comprising:
displaying the prescription pickup location as a first location when a payment transaction initiated by the mobile communication device is successful; and
displaying the prescription pickup location as a second location when the payment transaction is unsuccessful.

24. The method of claim 23, wherein the act of displaying the map of the pharmacy further comprises:
displaying the map including a route between a location of the mobile communication device and the first location or the second location.

25. The method of claim 19, wherein the information associated with the prescription order includes one of more of:
    user input received from the mobile communication device;
    payment information associated with the prescription order;
    a type of prescription drug associated with the prescription order; and
    a location of the mobile communication device.

* * * * *